US00PP23506P3

(12) United States Plant Patent
Ferguson et al.

(10) Patent No.: US PP23,506 P3
(45) Date of Patent: Apr. 2, 2013

(54) STRAWBERRY PLANT NAMED 'DRISSTRAWTWENTYONE'

(50) Latin Name: *Fragaria×ananassa*
Varietal Denomination: DrisStrawTwentyOne

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 33 days.

(21) Appl. No.: 13/136,089

(22) Filed: Jul. 22, 2011

(65) Prior Publication Data

US 2013/0025009 P1 Jan. 24, 2013

(51) Int. Cl.
*A01H 5/00* (2006.01)

(52) U.S. Cl. ..... Plt./209

(58) Field of Classification Search ..... Plt./209
See application file for complete search history.

*Primary Examiner* — Susan McCormick Ewoldt
(74) *Attorney, Agent, or Firm* — Jondle & Associates, P.C.

(57) ABSTRACT

A new and distinct variety of strawberry plant named 'DrisStrawTwentyOne' characterized by having large sized, biconical shaped berries that are dark red in color, and having a weak sweetness, is disclosed.

3 Drawing Sheets

Genus and species: *Fragaria×ananassa*.
Variety denomination: 'DrisStrawTwentyOne'.

BACKGROUND OF THE NEW PLANT

The present invention relates to a new and distinct strawberry variety designated 'DrisStrawTwentyOne' and botanically known as *Fragaria×ananassa*. This new strawberry variety was the result of a controlled cross conducted in Ventura Calif. in 2007 between the proprietary female parent '13H377' (unpatented) and the proprietary male parent '587L48' (unpatented). A single plant was selected for asexual propagation via tissue culture and vegetative cuttings in Shasta County, Calif. in 2008.

'DrisStrawTwentyOne' underwent further testing in Hillsborough, Fla. for four years (2007-2011). The present invention has been found to retain its distinctive characteristics through several asexual propagations via stolons.

Plant Breeder's Rights for this variety have not been applied for. 'DrisStrawTwentyOne' has not been made publicly available or sold more than one year prior to the filing date of this application.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
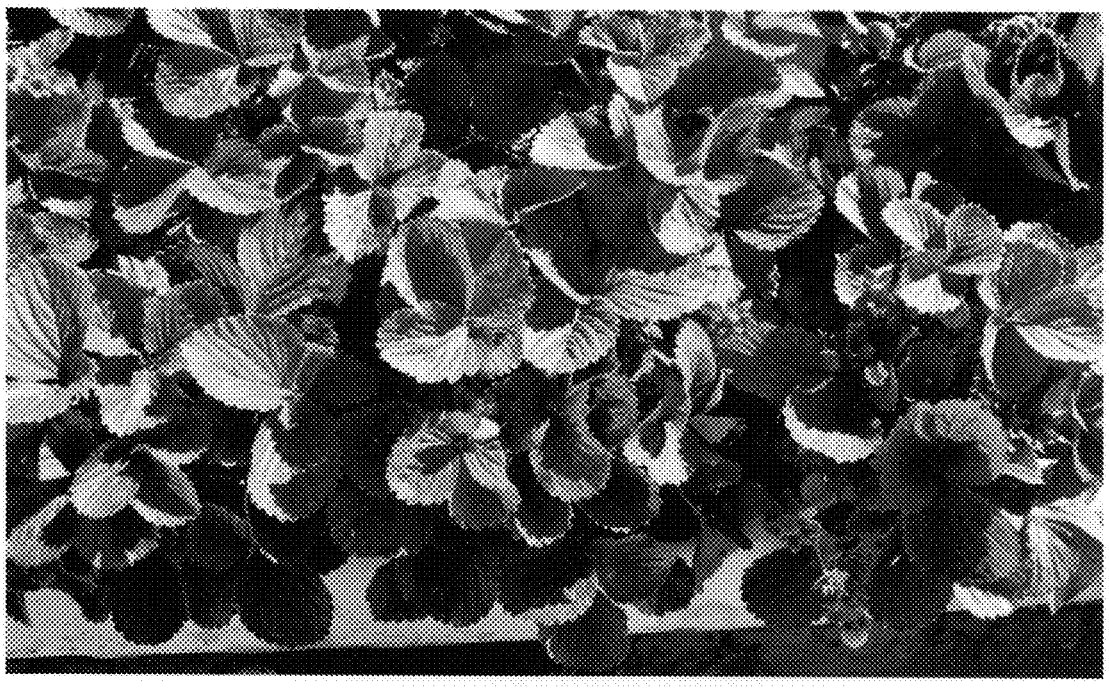
FIG. 1 shows overall plant habit including fruit at various stages of development.
Figure 2:
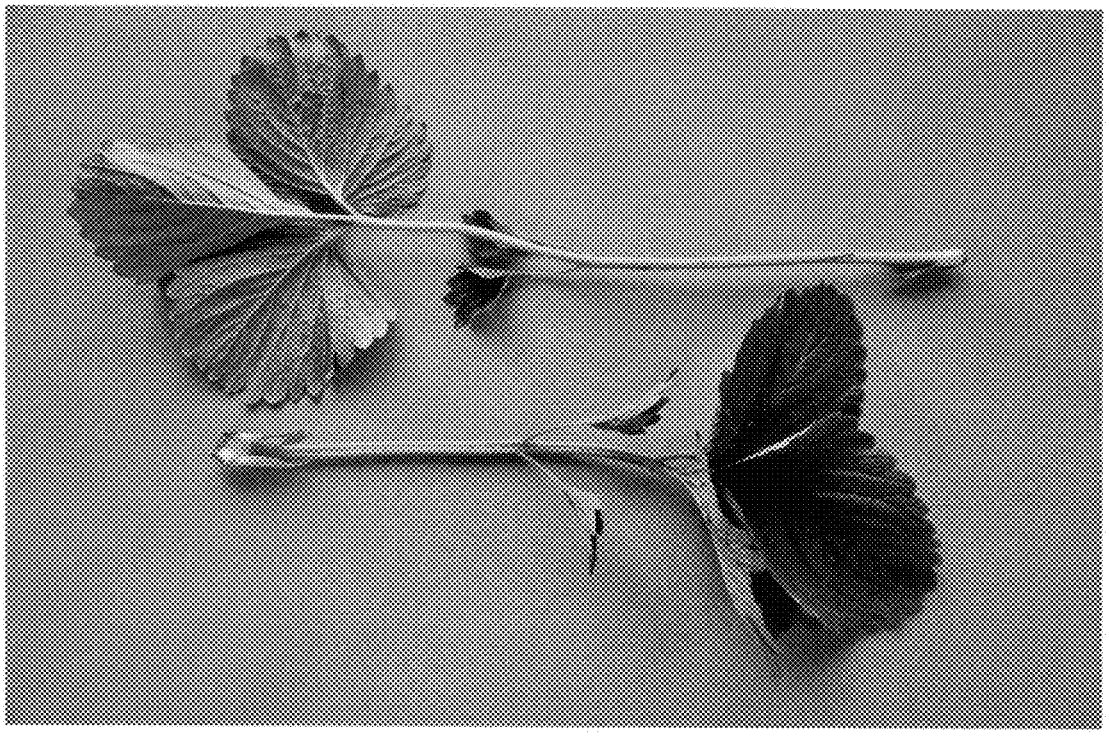
FIG. 2 shows leaves of the plant with three leaflets.
Figure 3:
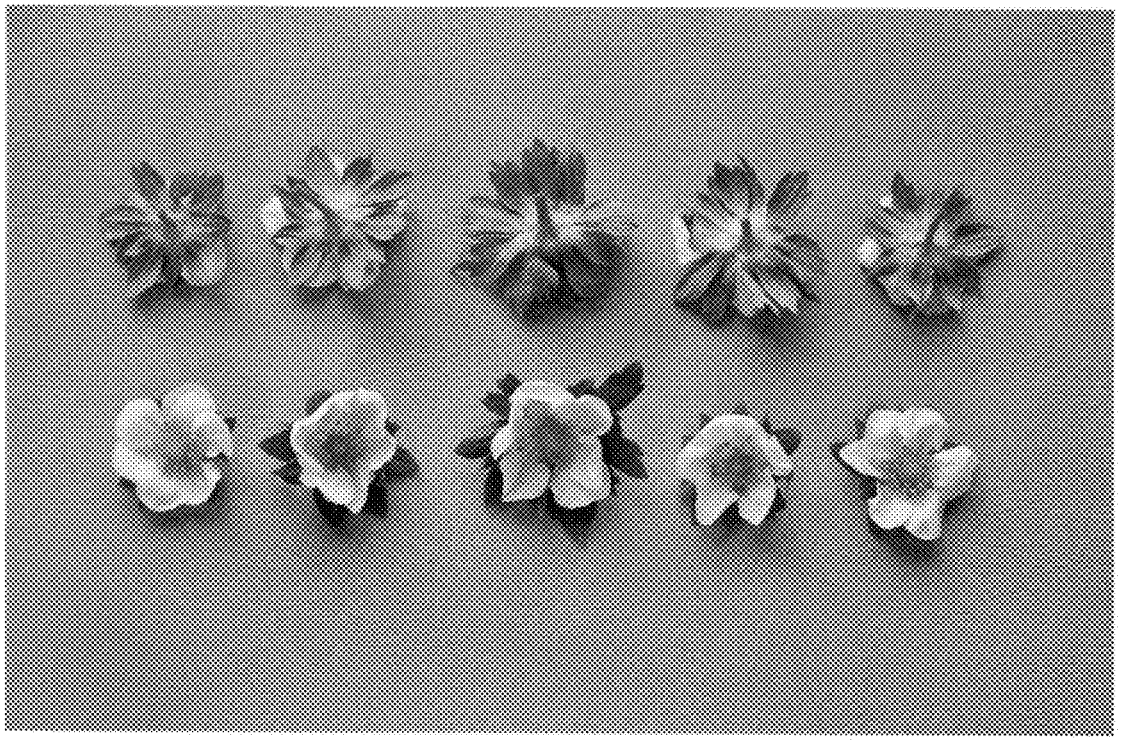
FIG. 3 shows the upper and lower surface of the flowers.
Figure 4:
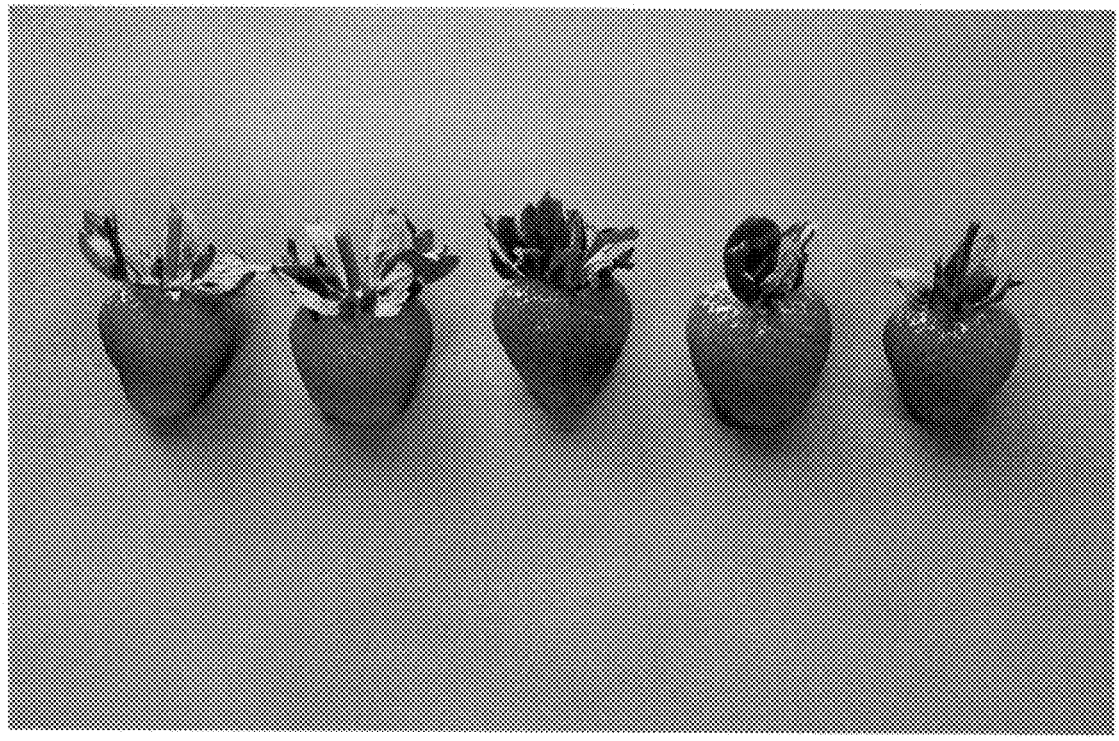
FIG. 4 shows the whole fruit.
Figure 5:
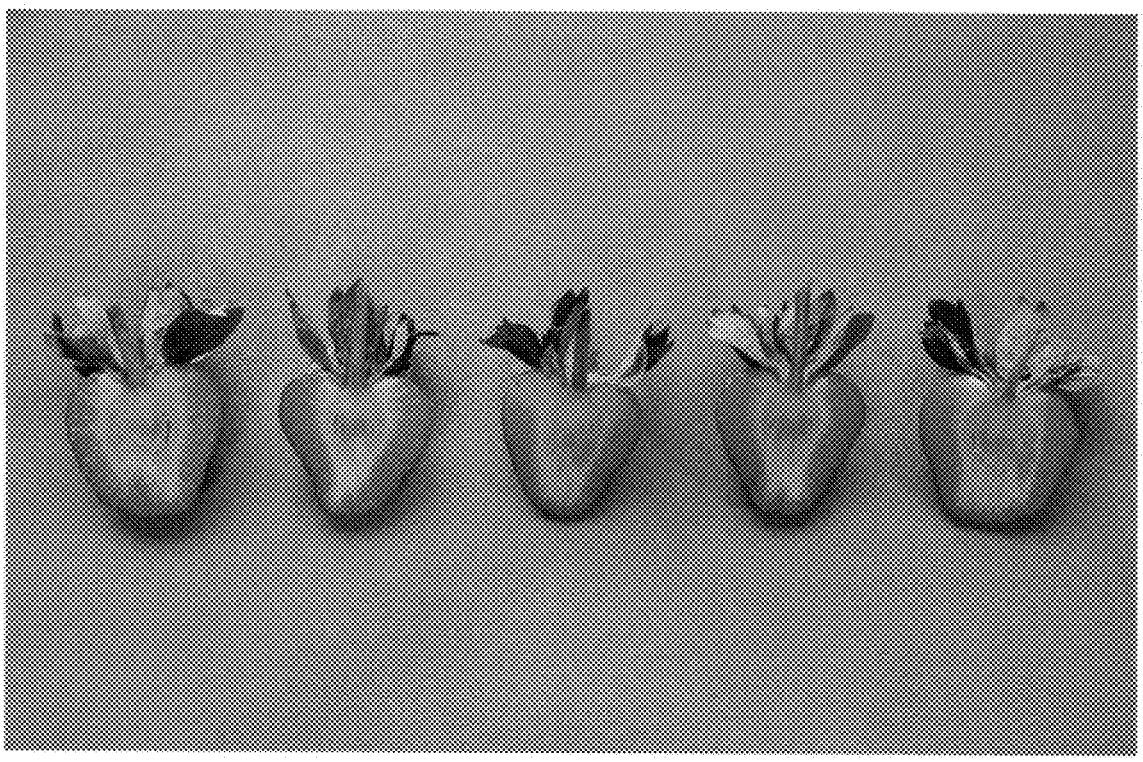
FIG. 5 shows the fruit in longitudinal cross-section.

The following detailed descriptions set forth the distinctive characteristics of 'DrisStrawTwentyOne'. The data which define these characteristics is based on observations taken in Ventura, Calif. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentyOne' has not been observed under all possible environmental conditions. The botanical description of 'DrisStrawTwentyOne' was taken from four-month-old plants. Color terminology follows The Royal Horticultural Society Colour Chart, London (R.H.S.) (2001).

DETAILED BOTANICAL DESCRIPTION OF THE PLANT

Classification:
- *Species.*—*Fragaria×ananassa.*
- *Common name.*—Strawberry.
- *Denomination.*—'DrisStrawTwentyOne'.

Parentage:
- *Female parent.*—The proprietary variety '13H377' (unpatented).
- *Male parent.*—The proprietary variety '587L48' (unpatented).

Plant:
- *Height.*—29.9 cm.
- *Diameter.*—47.0 cm.
- *Number of crowns/plant.*—4.
- *Habit.*—Upright.
- *Density of individual plant.*—Dense.
- *Vigor.*—Strong.

Leaves:
- *Leaf length.*—25.0 cm.
- *Leaf width.*—25.0 cm.
- *Terminal leaflet length.*—8.6 cm.
- *Terminal leaflet width.*—8.3 cm.
- *Terminal leaflet length/width ratio.*—1.0; as long as broad.
- *Number of teeth/terminal leaflet.*—28.

*Shape of teeth*.—Rounded-crenate.
*Color*.—Upper surface: Dark; RHS 147A (Dark yellow-green). Lower surface: Medium; RHS 148B (Medium yellow-green).
*Leaf shape in cross section*.—Concave.
*Leaf blistering*.—Medium.
*Leaf glossiness*.—Medium.
*Number of leaflets*.—3 only.
*Terminal leaflet margin profile*.—Flat (level with the leaflet blade).
*Terminal leaflet shape*.—Orbicular.
*Terminal leaflet base shape*.—Rounded.
*Terminal leaflet apex descriptor*.—Rounded.
*Terminal leaflet size*.—Large.
*Terminal leaflet variegation*.—Absent.
*Terminal leaflet margin*.—Crenate.

Petiole:
*Length*.—16.5 cm; Long.
*Diameter*.—3.29 mm.
*Pubescence*.—Lightly puberulent.
*Pose of hairs*.—Outwards — Horizontal.
*Color*.—RHS 144C (Medium yellow-green).

Petiolule:
*Color*.—RHS 144A (Medium yellow-green).
*Length*.—10.1 mm.
*Diameter*.—1.54 mm.
*Bract frequency*.—2.

Stipule:
*Length*.—28.7 mm.
*Width*.—7.03 mm.
*Pubescence*.—Dense.
*Stipule anthocyanin coloration*.—Absent or very weak.

Stolon:
*Number*.—Few.
*Average number of daughter plants per plant*.—28.
*Stolon anthocyanin coloration*.—Strong.
*Stolon anthocyanin color*.—RHS 45A (Dark red).
*Thickness*.—Medium.
*Pubescence*.—Sparse.

Inflorescence:
*Position relative to foliage*.—Beneath.
*Number of flowers*.—50.
*Time of flowering* (50% *of plants at first flower*).—May 1 to January 1.
*Flower size*.—Large.
*Diameter*.—28.62 mm.
*Petals*.—Shape: Orbicular. Apex: Rounded. Base: Concave-convex. Margin: Entire. Spacing: Overlapping. Length: 14.6 mm. Width: 14.8 mm. Length/width ratio: 1.0; as long as broad. Typical and observed petal number per flower: 6. Color (upper surface): RHS 155D (White).
*Calyx*.—Diameter: 36.55 mm. Diameter relative to corolla: Larger. Inner calyx diameter relative to outer: Same size.
*Sepal*.—Shape: Elliptical. Apex: Convex. Margin: Entire. Length: 14.29 mm. Width: 6.97 mm. Typical and observed sepal number per flower: 12. Receptacle color: RHS 1B (Medium green-yellow). Anther color: RHS 163A (Medium greyed-orange). Stamen: Present.
*Pedicel*.—Attitude of hairs: Upwards.

Fruiting truss:
*Length*.—22.3 cm; Long.
*Diameter at base of truss*.—3.2 mm.
*Number of berries per fruiting truss*.—3.
*Attitude at first picking*.—Prostrate.
*Color at base of truss*.—RHS 144B (Medium yellow-green).

Fruit:
*Length*.—48.91 mm.
*Width*.—47.67 mm.
*Length/width ratio*.—1.0.
*Fruit hollow length*.—10.26 mm.
*Fruit hollow width*.—12.38 mm.
*Fruit hollow length/width ration*.—0.8.
*Fruit hollow center* (*cavity*).—Small.
*Weight* (*per individual berry*).—30.8 g.
*Fruit ratio of length/maximum width*.—As long as broad.
*Relative fruit size*.—Large.
*Predominant fruit shape*.—Bi-conical.
*Difference in shape between primary and secondary fruits*.—None or very slight.
*Unevenness of fruit surface*.—Slightly uneven.
*Fruit skin color*.—RHS 46A (Dark red).
*Evenness of fruit color*.—Even or very slightly uneven.
*Fruit glossiness*.—Medium.
*Insertion of achenes*.—Below surface.
*Achene coloration* (*sunward side of berry*).—RHS 185C (Medium greyed-purple).
*Achene coloration* (*shaded side of berry*).—RHS 153C (Medium yellow-green).
*Achenes per berry*.—417.
*Achene weight* (*weight of achenes in grams divided by total # seed*).—0.000706761 g.
*Band without achenes*.—Absent or very narrow.
*Insertion of calyx*.—In a basin — inserted.
*Pose of calyx segments*.—Reflexed — upwards.
*Size of calyx in relation to fruit*.—Much larger.
*Adherence of calyx*.—Medium.
*Firmness of flesh*.—Medium.
*Color of flesh* (*excluding core*).—RHS 155B (White) and RHS 44B (Medium-red).
*Color of core*.—RHS 155B (White) and RHS 41B (Light Red).
*Evenness of flesh color*.—Slightly uneven.
*Distribution of flesh color*.—Only marginal.
*Sweetness*.—Weak.
*Acidity*.—Medium.
*Texture when tasted*.—Average, between fine and coarse.
*Type of bearing*.—Fully everbearing fully remontant.
*Grams of fruit/plant*.—487.0.
*Harvest interval*.—Late September to mid-January.
*Harvest maturity*.—Late.

COMPARISON WITH PARENTAL AND COMMERCIAL VARIETIES

When 'DrisStrawTwentyOne' is compared to the proprietary female parent '13H377' (unpatented), 'DrisStrawTwentyOne' is more vigorous, has higher yields, later fruit production pattern, larger fruit size and improved fruit appearance than '13H377'.

When 'DrisStrawTwentyOne' is compared to the proprietary male parent '587L48' (unpatented), 'DrisStrawTwentyOne' is less vigorous, has higher yields, larger fruit size and improved fruit appearance than '587L48'.

When 'DrisStrawTwentyOne' is compared to the commercial variety 'Driscoll El Dorado' (U.S. Plant Pat. No. 16,238), 'DrisStrawTwentyOne' has an upright growth habit, and fruit having a bi-conical shape, light red core, and medium flesh, while 'Driscoll El Dorado' has a globose growth habit, and fruit having a conical shape, orange red core, and firm flesh.

When 'DrisStrawTwentyOne' is compared to the commercial variety 'DrisStrawEight' (U.S. Plant Pat. No. 20,735), 'DrisStrawTwentyOne' has an upright growth habit, strong vigor, and fruit having a bi-conical shape, dark red color, and medium flesh, while 'DrisStrawEight' has a globose growth habit, medium vigor, and fruit having a conical and almost cylindrical shape, medium red color and firm flesh.

We claim:

1. A new and distinct variety of strawberry plant as described and shown herein.

* * * * *

UNITED STATES PATENT AND TRADEMARK OFFICE

CERTIFICATE OF CORRECTION

PATENT NO. : PP23,506 P3
APPLICATION NO. : 13/136089
DATED : April 2, 2013
INVENTOR(S) : Michael D. Ferguson and Terrance C. Moran It is certified that error appears in the above-identified patent and that said Letters Patent is hereby corrected as shown below:

In the Specifications:

Column 1, line 9: "Ventura, California" should read --Ventura County, California--.

Column 1, lines 14-15: "Hillsborough, Florida" should read --Ventura County, California--.

Column 2, line 2: "Ventura, California" should read --Ventura County, California--.

Signed and Sealed this
Twenty-eighth Day of May, 2013

Teresa Stanek Rea
*Acting Director of the United States Patent and Trademark Office*